United States Patent
Dandala et al.

(10) Patent No.: US 10,370,329 B2
(45) Date of Patent: Aug. 6, 2019

(54) PROCESS FOR THE ENANTIOMERIC RESOLUTION OF APREMILAST INTERMEDIATES

(71) Applicant: Mylan Laboratories Limited, Hyderabad (IN)

(72) Inventors: Ramesh Dandala, Hyderabad (IN); Sureshbabu Jayachandra, Maharashtra (IN); Vipin Kumar Kaushik, Hyderabad (IN); Nageshwara Rao Achanta, Hyderabad (IN); Sivaprasad Dorasala, Maharashtra (IN)

( * ) Notice: Subject to any disclaimer, the term of this patent is extended or adjusted under 35 U.S.C. 154(b) by 0 days.

(21) Appl. No.: 15/573,290

(22) PCT Filed: Apr. 22, 2016

(86) PCT No.: PCT/IN2016/050119
§ 371 (c)(1),
(2) Date: Nov. 10, 2017

(87) PCT Pub. No.: WO2016/174685
PCT Pub. Date: Nov. 3, 2016

(65) Prior Publication Data
US 2018/0134660 A1  May 17, 2018

(30) Foreign Application Priority Data
Apr. 27, 2015  (IN) .......................... 2143/CHE/2015

(51) Int. Cl.
| | |
|---|---|
| *C07C 315/06* | (2006.01) |
| *C07D 209/48* | (2006.01) |
| *C07C 311/19* | (2006.01) |
| *C07C 317/28* | (2006.01) |
| *C07C 69/76* | (2006.01) |
| *C07C 315/04* | (2006.01) |

(52) U.S. Cl.
CPC ............ *C07D 209/48* (2013.01); *C07C 69/76* (2013.01); *C07C 311/19* (2013.01); *C07C 315/04* (2013.01); *C07C 315/06* (2013.01); *C07C 317/28* (2013.01); *C07B 2200/07* (2013.01)

(58) Field of Classification Search
CPC ... C07C 311/19; C07C 315/04; C07C 315/06; C07C 317/28
See application file for complete search history.

(56) References Cited

U.S. PATENT DOCUMENTS

| | | | | |
|---|---|---|---|---|
| 6,020,358 A | * | 2/2000 | Muller ............... | A61K 31/4035 514/411 |
| 8,455,536 B2 | * | 6/2013 | Muller ............... | A61K 31/4035 514/417 |
| 9,944,599 B2 | * | 4/2018 | Stavber ................ | C07C 315/04 |
| 2004/0171838 A1 | * | 9/2004 | Meyer .................. | C07D 405/12 546/281.7 |
| 2011/0218360 A1 | * | 9/2011 | Cherukupally ....... | C07C 209/28 564/304 |
| 2013/0217918 A1 | * | 8/2013 | Venkateswaralu .... | C07C 315/04 564/340 |
| 2013/0345282 A1 | * | 12/2013 | Liu ....................... | C07D 209/46 514/417 |
| 2014/0081032 A1 | * | 3/2014 | Connolly ............. | C07D 209/48 548/478 |
| 2017/0057916 A1 | * | 3/2017 | Fang .................... | C07D 209/50 |

FOREIGN PATENT DOCUMENTS

| | | | | |
|---|---|---|---|---|
| WO | WO-0025777 A1 | * | 5/2000 | ......... A61K 31/4035 |
| WO | WO-03080049 A1 | * | 10/2003 | ......... A61K 31/4035 |
| WO | WO-2005030730 A1 | * | 4/2005 | ........... C07D 223/12 |
| WO | WO-2010059913 A2 | * | 5/2010 | ........... C07C 209/28 |
| WO | WO-2016146990 A1 | * | 9/2016 | ........... C07D 209/48 |
| WO | WO-2016161996 A1 | * | 10/2016 | ........... C07C 315/06 |
| WO | WO-2017094031 A2 | * | 6/2017 | ........... C07D 209/48 |

* cited by examiner

*Primary Examiner* — Nyeemah A Grazier

(57) ABSTRACT

A process for the resolution of racemic 2-(3-ethoxy-4-methoxyphenyl)-1-(methylsulphonyl)-eth-2-ylamine using novel chiral salts is disclosed. An L-phenylalanine p-toluene-sulfonamide salt of (S)-2-(3-ethoxy-4-methoxyphenyl)-1-(methylsulphonyl)-eth-2-ylamine and a di-p-toluoyl-L-tartaric acid salt of (S)-2-(3-ethoxy-4-methoxyphenyl)-1-(methylsulphonyl)-eth-2-ylamine are also provided.

4 Claims, No Drawings

PROCESS FOR THE ENANTIOMERIC RESOLUTION OF APREMILAST INTERMEDIATES

CROSS-REFERENCE TO RELATED APPLICATIONS

This application claims the benefit of Indian Provisional Patent Application No. 2143/CHE/2015 filed on Apr. 27, 2015, which is hereby incorporated by reference in its entirety.

BACKGROUND OF THE INVENTION

Field of the Invention

The present disclosure relates generally to the preparation of apremilast and intermediates thereof. In particular, the present disclosure provides a method for the resolution of racemic 2-(3-ethoxy-4-methoxyphenyl)-1-(methylsulphonyl)-eth-2-ylamine using novel chiral salts.

Background of the Invention

Apremilast is chemically known as N-[2-[(1S)-1-(3-ethoxy-4-methoxyphenyl)-2-(methylsulfonyl)ethyl]-2,3-dihydro-1,3-dioxo-1H-isoindol-4-yl]acetamide and is shown in Formula I below. Apremilast is a phosphodiesterase 4 (PDE4) inhibitor and is useful in the treatment of severe plaque psoriasis and psoriatic arthritis.

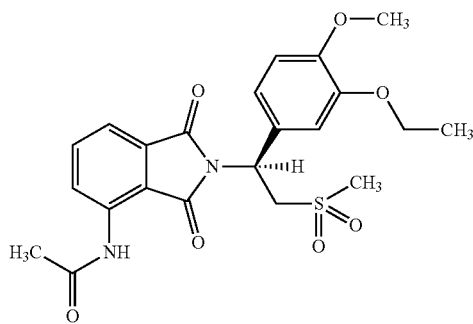

Formula I

U.S. Pat. No. 7,427,638 discloses apremilast and a process for the preparation thereof.

2-(3-Ethoxy-4-methoxyphenyl)-1-(methylsulphonyl)-eth-2-ylamine may be used as an intermediate in the preparation of apremilast. It is desirable to synthesize this compound as the S enantiomeric form, however, often a racemic mixture is produced instead. The present invention provides a process for the resolution of racemic 2-(3-ethoxy-4-methoxyphenyl)-1-(methylsulphonyl)-eth-2-ylamine. 2-(3-Ethoxy-4-methoxyphenyl)-1-(methylsulphonyl)-eth-2-ylamine may then be further converted to apremilast.

SUMMARY OF THE INVENTION

One aspect of the present invention provides a process for the preparation of (S)-2-(3-ethoxy-4-methoxyphenyl)-1-(methylsulphonyl)-eth-2-ylamine, comprising the steps of:

a. dissolving a racemic mixture of 2-(3-ethoxy-4-methoxyphenyl)-1-(methylsulphonyl)-eth-2-ylamine in an organic solvent to form a solution;

b. adding L-phenylalanine p-toluene sulfonamide or di-p-toluoyl-L-tartaric acid to the solution; and c. isolating a chiral salt of (S)-2-(3-ethoxy-4-methoxyphenyl)-1-(methylsulphonyl)-eth-2-ylamine.

According to this embodiment, the organic solvent may be an alcoholic solvent, for example, methanol, ethanol, or isopropanol. In some embodiments, the alcoholic solvent is methanol.

Within the context of the present invention, if L-phenylalanine p-toluene sulfonamide is added to the solution in step b, an L-phenylalanine p-toluene sulfonamide salt of (S)-2-(3-ethoxy-4-methoxyphenyl)-1-(methylsulphonyl)-eth-2-ylamine may be isolated. Similarly, if di-p-toluoyl-L-tartaric acid is added to the solution in step b, a di-p-toluoyl-L-tartaric acid salt of (S)-2-(3-ethoxy-4-methoxyphenyl)-1-(methylsulphonyl)-eth-2-ylamine may be isolated.

Within the context of the present invention, the L-phenylalanine p-toluene sulfonamide salt of (S)-2-(3-ethoxy-4-methoxyphenyl)-1-(methylsulphonyl)-eth-2-ylamine or the di-p-toluoyl-L-tartaric acid salt of (S)-2-(3-ethoxy-4-methoxyphenyl)-1-(methylsulphonyl)-eth-2-ylamine may be further converted to apremilast or a pharmaceutically acceptable salt thereof.

DETAILED DESCRIPTION OF THE INVENTION

It is to be understood that the description of the present invention has been simplified to illustrate elements that are relevant for a clear understanding of the invention, while eliminating, for purposes of clarity, other elements that may be well known.

One aspect of the present invention provides novel chiral salts of (S)-2-(3-ethoxy-4-methoxyphenyl)-1-(methylsulphonyl)-eth-2-ylamine (Formula-II).

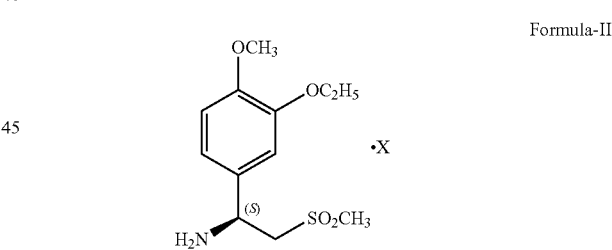

Formula-II

Within the context of this embodiment, X is L-phenylalanine p-toluenesulfonamide or di-p-toluoyl-L-tartaric acid, shown below:

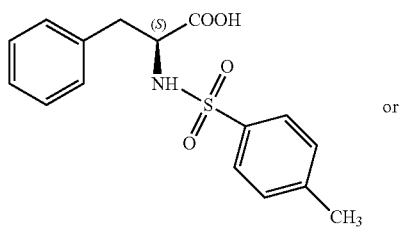

L-Phenylalanine p-toluenesulfonamide or

-continued

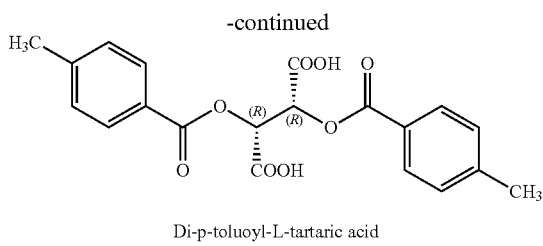

Di-p-toluoyl-L-tartaric acid

One embodiment of the present invention provides an L-phenylalanine p-toluenesulfonamide salt of (S)-2-(3-ethoxy-4-methoxyphenyl)-1-(methylsulphonyl)-eth-2-ylamine.

Another embodiment of the present invention provides a di-p-toluoyl-L-tartaric acid salt of (S)-2-(3-ethoxy-4-methoxyphenyl)-1-(methylsulphonyl)-eth-2-ylamine.

Another aspect of the present invention provides a process for the resolution of racemic 2-(3-ethoxy-4-methoxyphenyl)-1-(methylsulphonyl)-eth-2-ylamine by converting the racemic mixture of 2-(3-ethoxy-4-methoxyphenyl)-1-(methylsulphonyl)-eth-2-ylamine into a chiral salt.

In one embodiment, the undesired R enantiomer of 2-(3-ethoxy-4-methoxyphenyl)-1-(methylsulphonyl)-eth-2-ylamine may be substantially removed from a racemic mixture of 2-(3-ethoxy-4-methoxyphenyl)-1-(methylsulphonyl)-eth-2-ylamine by converting the racemic mixture of 2-(3-ethoxy-4-methoxyphenyl)-1-(methylsulphonyl)-eth-2-ylamine into an L-phenylalanine p-toluenesulfonamide salt of (S)-2-(3-ethoxy-4-methoxyphenyl)-1-(methylsulphonyl)-eth-2-ylamine.

In another embodiment, the undesired R enantiomer of 2-(3-ethoxy-4-methoxyphenyl)-1-(methylsulphonyl)-eth-2-ylamine may be substantially removed from a racemic mixture of 2-(3-ethoxy-4-methoxyphenyl)-1-(methylsulphonyl)-eth-2-ylamine by converting the racemic mixture of 2-(3-ethoxy-4-methoxyphenyl)-1-(methylsulphonyl)-eth-2-ylamine into an a di-p-toluoyl-L-tartaric acid salt of (S)-2-(3-ethoxy-4-methoxyphenyl)-1-(methylsulphonyl)-eth-2-ylamine.

According to this embodiment, a chiral salt of 2-(3-ethoxy-4-methoxyphenyl)-1-(methylsulphonyl)-eth-2-ylamine may be prepared by the following steps:
 a. dissolving a racemic mixture of 2-(3-ethoxy-4-methoxyphenyl)-1-(methylsulphonyl)-eth-2-ylamine in an organic solvent to form a solution;
 b. adding L-phenylalanine p-toluene sulfonamide or di-p-toluoyl-L-tartaric acid to the solution; and
 c. isolating a chiral salt of (S)-2-(3-ethoxy-4-methoxyphenyl)-1-(methylsulphonyl)-eth-2-ylamine.

According to the present embodiment, a racemic mixture of 2-(3-ethoxy-4-methoxyphenyl)-1-(methylsulphonyl)-eth-2-ylamine may be dissolved in an organic solvent to form a solution.

Within the context of this embodiment, the racemic mixture of 2-(3-ethoxy-4-methoxyphenyl)-1-(methylsulphonyl)-eth-2-ylamine may be prepared by prior art processes, for example, those disclosed in U.S. Pat. No. 6,020,358 or International Patent Application Publication No. WO 2013126360. The processes disclosing the preparation of racemic 2-(3-ethoxy-4-methoxyphenyl)-1-(methylsulphonyl)-eth-2-ylamine in each reference are incorporated herein by reference.

Within the context of this embodiment, the solvent may be an alcoholic solvent, for example, methanol, ethanol, isopropanol, or mixtures thereof. In some particularly useful embodiments, methanol is used.

Next, L-phenylalanine p-toluenesulfonamide or di-p-toluoyl-tartaric acid may be added to the solution.

A chiral salt of (S)-2-(3-ethoxy-4-methoxyphenyl)-1-(methylsulphonyl)-eth-2-ylamine may then be isolated. For example, if L-phenylalanine p-toluenesulfonamide was added to the solution, the L-phenylalanine p-toluenesulfonamide salt of (S)-2-(3-ethoxy-4-methoxyphenyl)-1-(methylsulphonyl)-eth-2-ylamine may be isolated. Similarly, if di-p-toluoyl-tartaric acid was added to the solution, a di-p-toluoyl-tartaric acid salt of (S)-2-(3-ethoxy-4-methoxyphenyl)-1-(methylsulphonyl)-eth-2-ylamine may be isolated.

Isolation of the chiral salt from the solution may be carried out by a variety of methods well known in the art.

For example, in some particularly useful embodiments, the solution is heated to reflux. One of skill in the art, upon carrying out this step, will recognize at what temperature reflux conditions are achieved. Within the context of this embodiment, heating the solution to reflux may cause a precipitate to form, creating a suspension.

Next, the suspension may then be cooled. In some embodiments, the suspension is cooled to about 30° C. to about 50° C. Isolation of the chiral salt of (S)-2-(3-ethoxy-4-methoxyphenyl)-1-(methylsulphonyl)-eth-2-ylamine may then be carried out, for example, by filtering the suspension to give a solid. The solid may optionally be further treated, for example, by further washing with a solvent or by drying, to improve purity.

Another aspect of the present invention provides a process for conversion of a chiral salt of (S)-2-(3-ethoxy-4-methoxyphenyl)-1-(methylsulphonyl)-eth-2-ylamine to apremilast. This may be carried out according to methods disclosed in prior art, for example, in U.S. Pat. No. 7,427,638.

An example of one embodiment by which this process may be carried out is depicted in Scheme-I below.

Scheme-I

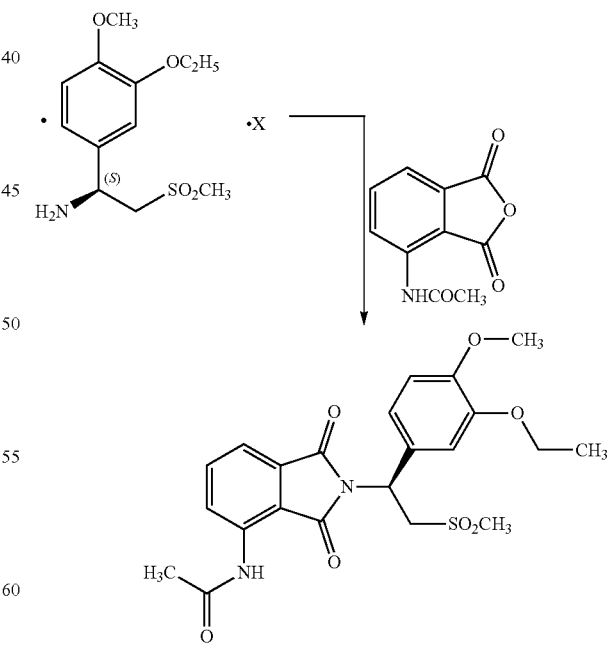

Apremilast

Within the context of this embodiment, X is L-phenylalanine p-toluenesulfonamide or di-p-toluoyl-L-tartaric acid, shown below:

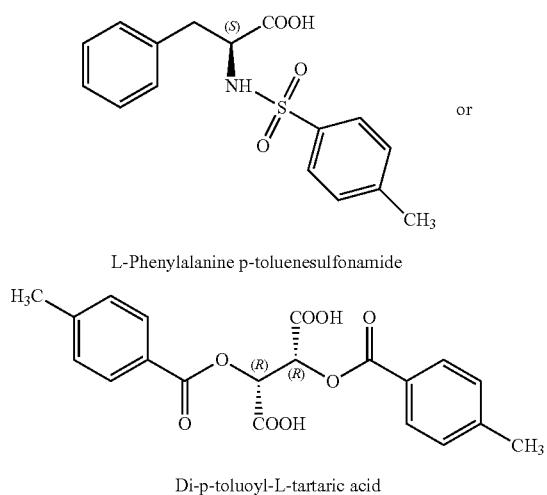

L-Phenylalanine p-toluenesulfonamide

Di-p-toluoyl-L-tartaric acid

According to this embodiment, the chiral salt of (S)-2-(3-ethoxy-4-methoxyphenyl)-1-(methylsulphonyl)-eth-2-ylamine may be reacted with 3-acetamidophthalic anhydride to yield apremilast.

Within the context of this embodiment, the reaction of (S)-2-(3-ethoxy-4-methoxyphenyl)-1-(methylsulphonyl)-eth-2-ylamine with 3-acetamidophthalic anhydride may be carried out in the presence of a solvent. The solvent may be, for example, toluene or acetic acid.

Next, apremilast may be isolated. This may be carried out by methods well known in the art. For example, the reaction mass may be heated to reflux, which may result in formation of a solid. In some embodiments, the reaction mass is heated to reflux.

Another aspect of the present invention provides a method for conversion of a racemic mixture of 2-(3-ethoxy-4-methoxyphenyl)-1-(methylsulphonyl)-eth-2-ylamine to apremilast, which may be carried out as depicted below in Scheme-II.

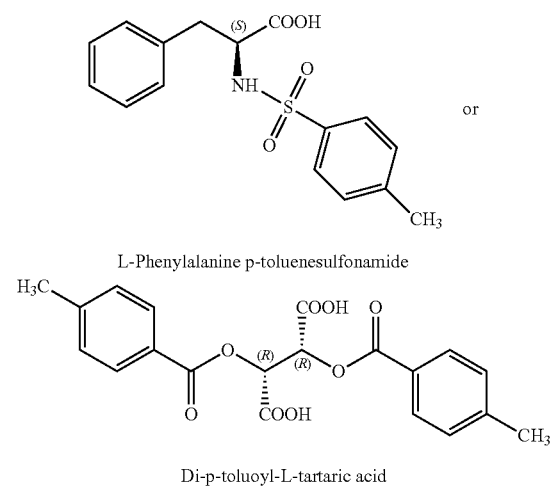

Scheme-II

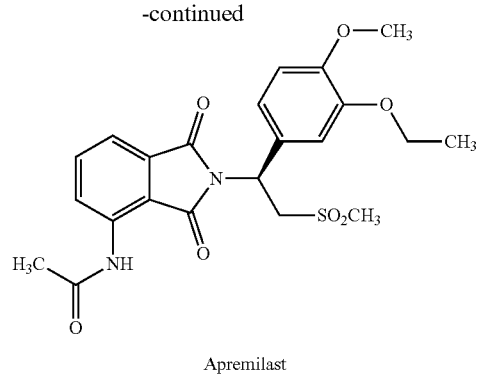

Apremilast

Within the context of this embodiment, X is L-phenylalanine p-toluenesulfonamide or di-p-toluoyl-L-tartaric acid, shown below:

L-Phenylalanine p-toluenesulfonamide

Di-p-toluoyl-L-tartaric acid

Within the context of this embodiment, each step depicted in Scheme-II may be carried out as described above. The apremilast may optionally be further converted to a pharmaceutically acceptable salt of apremilast as disclosed above.

In view of the above description and the examples below, one of ordinary skill in the art will be able to practice the invention as claimed without undue experimentation. The foregoing will be better understood with reference to the following examples that detail certain procedures for the preparation of molecules according to the present invention. All references made to these examples are for the purposes of illustration. The following examples should not be considered exhaustive, but merely illustrative of only a few of the many aspects and embodiments contemplated by the present disclosure.

EXAMPLES

Example 1: Preparation of 3-ethoxy-4-methoxybenzonitrile

A solution of 3-ethoxy-4-methoxybenzaldehyde (100 g, 555 mmol) and hydroxylamine hydrochloride (46.27 g, 665 mmol) in acetonitrile (500 mL) was heated to reflux and stirred. After completion of the reaction, the reaction mass was concentrated under reduced pressure to yield an oil. The obtained oil was crystallized in water (500 mL) to yield 3-ethoxy-4-methoxybenzonitrile.

Example 2: Preparation of 2-(3-ethoxy-4-methoxyphenyl)-1-(methylsulphonyl)-eth-2-ylamine n-Butyllithium in tetrahydrofuran (1.6 M, 425 mL) was added to a solution of methylsulfonylmethane (58.43 g, 620 mmol) in tetrahydrofuran (600 mL) at 0-5° C. and the resulting mixture was stirred at this temperature for 90 minutes. A solution of 3-ethoxy-4-methoxy benzonitrile (100 g, 564 mmol) in tetrahydrofuran (400 mL) was then added at 0-5° C. and the temperature was raised to 25-30° C. The reaction mixture was stirred for 90 min at this temperature. After completion of reaction, sodium borohydride (27.6 g, 729 mmol) in five equal lots was added into reaction mass at 0-5° C. Acetic acid (150 mL) was added slowly and the reaction mass was stirred overnight at 0-5° C. After completion of reaction, aqueous sodium hydroxide solution (760 mL, 10% w/v) was added and the temperature was raised to 50-55° C. After 16 hours of stirring, the reaction mass was cooled and diluted with water (1.6 L). The resulting suspension was stirred at 0-5° C. for 24 hours then filtered to yield 2-(3-ethoxy-4-methoxyphenyl)-1-(methylsulphonyl)-eth-2-ylamine, which was purified with ethyl acetate.

Example 3: Preparation of (S)-2-(3-ethoxy-4-methoxyphenyl)-1-(methylsulphonyl)-eth-2-ylamine L-phenylalanine p-toluenesulfonamide Salt 2-(3-Ethoxy-4-methoxyphenyl)-1-(methylsulphonyl)-eth-2-ylamine (100.0 g, 366 mmol) was added to methanol (1.8 L) and the solution was stirred for 10 minutes at 45° C. L-phenylalanine p-toluenesulfonamide (64.3 g, 201 mmol) was then added and the solution was stirred at reflux temperature for 90 minutes. The obtained suspension was allowed to cool to 45° C. while stirring for 4 hours. The suspension was filtered to obtain a solid which was then washed with methanol (200 mL) and dried to yield crude (S)-2-(3-ethoxy-4-methoxyphenyl)-1-(methylsulphonyl)-eth-2-ylamine L-phenylalanine p-toluenesulfonamide salt with a chiral purity of 97.66%.

The obtained crude (S)-2-(3-ethoxy-4-methoxyphenyl)-1-(methylsulphonyl)-eth-2-ylamine-L-phenylalanine p-toluenesulfonamide salt was then added to methanol (1 L) and the solution was refluxed for 90 minutes. The reaction mixture was cooled to 30° C. and stirred for 4 hours. The obtained suspension was filtered to obtain a solid which was then washed with methanol (200 mL) and dried to yield (S)-2-(3-ethoxy-4-methoxyphenyl)-1-(methylsulphonyl)-eth-2-ylamine L-phenylalanine p-toluenesulfonamide salt having a chiral purity of >99.5%.

Example 4: Preparation of (S)-2-(3-ethoxy-4-methoxyphenyl)-1-(methylsulphonyl)-eth-2-ylamine Di-p-toluoyl-L-tartaric Acid 2-(3-Ethoxy-4-methoxyphenyl)-1-(methylsulphonyl)-eth-2-ylamine (100.0 g, 365 mmol) was added to methanol (1.8 mL) and stirred for 10 minutes at 45° C. Di-p-toluoyl-L-tartaric acid (98.9 g, 256 mmol) was added and stirred at reflux temperature for 60 minutes. The obtained suspension was allowed to cool to 33° C. and stirred for 90 minutes. The suspension was filtered to obtain a solid which was washed with methanol (200 mL) and dried to yield crude (S)-2-(3-ethoxy-4-methoxyphenyl)-1-(methylsulphonyl)-eth-2-ylamine di-p-toluoyl-L-tartaric acid salt having a chiral purity of 78.59%.

The obtained crude (S)-2-(3-ethoxy-4-methoxyphenyl)-1-(methylsulphonyl)-eth-2-ylamine di-p-toluoyl-L-tartaric acid salt was added to methanol (800 mL) and refluxed for 90 minutes. The reaction mixture was cooled to 33° C. and stirred for 60 minutes. The suspension was filtered to obtain a solid which was washed with methanol (200 mL) and dried to yield (S)-2-(3-ethoxy-4-methoxyphenyl)-1-(methylsulphonyl)-eth-2-ylamine di-p-toluoyl-L-tartaric acid having a chiral purity of 91.39%.

Example 5: Preparation of N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast)

A suspension of (S)-2-(3-ethoxy-4-methoxyphenyl)-1-(methylsulphonyl)-eth-2-ylamine L-phenylalanine p-toluenesulfonamide (100 g, 169 mmol) and 3-acetamidophthalic anhydride (38.16 g, 186 mmol) in toluene (700 mL) was heated to reflux and stirred for 3 hours. The reaction mass was then concentrated under reduced pressure and the obtained residue was dissolved in methylene chloride (800 mL), washed with water (1 L), then with aqueous sodium bicarbonate solution (1 L, ~8% w/v) and finally with water (1 L). The aqueous and organic layers were separated and the organic layer was concentrated. N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast) was then crystallized from a mixture of ethanol and acetone.

Example 6: Preparation of N-[2-[(1S)-1-(3-Ethoxy-4-methoxyphenyl)-2-(methylsulfonyl)ethyl]-2,3-dihydro-1,3-dioxo-1H-isoindol-4-yl]acetamide (apremilast)

A suspension of (S)-2-(3-ethoxy-4-methoxyphenyl)-1-(methylsulphonyl)-eth-2-ylamine L-phenylalanine p-toluenesulfonamide (100 g, 169 mmol) and 3-acetamidophthalic anhydride (38.16 g, 186 mmol) in acetic acid (1 L) was heated to reflux and stirred for 15 hours. The reaction mass was concentrated under reduced pressure and the obtained residue was dissolved in ethyl acetate (1 L), washed with water (1 L), then aqueous sodium bicarbonate solution (1 L, 8% w/v), and finally with saturated sodium chloride solution (1 L). The aqueous and organic layers were separated and the organic layer was concentrated. N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast) was crystallized from a mixture of ethanol and acetone.

Example 7: Preparation of 3-Acetamidophthalic Anhydride

Step-I:
3-Nitrophthalic acid (100 g, 474 mmol) in ethanol (1.5 L) was hydrogenated using 10% Pd/C (10 g) at 25-30° C. by applying pressure of 2-3 kg/cm$^2$. After completion of the reaction, the solution was filtered and the obtained filtrate was concentrated under reduced pressure. The resulting solid was stirred in diisopropyl ether, and the solution was filtered to yield 3-aminophthalic acid.

Step-II:
A solution of 3-aminophthalic acid (100 g, 552 mmol) in acetic anhydride (300 mL) was heated to 110° C. The reaction mass cooled to 25-30° C. while being stirred then further cooled to 10° C. The crystalline solid obtained was collected by filtration and washed with hexane to yield 3-acetamidophthalic anhydride.

Example 8: Preparation of L-Phenylalanine p-Toluenesulfonamide

Aqueous sodium hydroxide (53 g, 1.325 mole dissolved in 175 mL of water) and p-toluenesulfonyl chloride (126.77 g, 665 mmole) were added sequentially to a suspension of L-phenylalanine (100 g, 605 mmole) in water (1.5 L) at 25-30° C. Thereafter, the reaction mass temperature was raised to 35-40° C. and the solution was stirred for six hours. After completion of the reaction, hydrochloric acid (~32% w/w, 125 mL) was added and a solid was precipitated. The solution was filtered to obtain a solid which was purified in methanol to yield L-phenylalanine p-toluenesulfonamide.

We claim:

1. A process for the preparation of (S)-2-(3-ethoxy-4-methoxyphenyl)-1-(methylsulphonyl)-eth-2-ylamine, comprising the steps of:

a. dissolving a racemic mixture of 2-(3-ethoxy-4-methoxyphenyl)-1-(methyl sulphonyl)-eth-2-ylamine in an organic solvent to form a solution;

b. adding L-phenylalanine p-toluene sulfonamide to the solution; and c. isolating a L-phenylalanine p-toluene sulfonamide salt of (S)-2-(3-ethoxy-4-methoxyphenyl)-1-(methylsulphonyl)-eth-2-ylamine, wherein the chiral salt of (S)-2-(3-ethoxy-4-methoxyphenyl)-1-(methylsulphonyl)-eth-2-ylamine is further converted into apremilast.

2. The process according to claim 1, wherein the organic solvent is an alcoholic solvent.

3. The process according to claim 2, wherein the alcoholic solvent is methanol.

4. A L-phenylalanine p-toluene-sulfonamide salt of (S)-2-(3-ethoxy-4-methoxyphenyl)-1-(methylsulphonyl)-eth-2-ylamine.

* * * * *